(12) United States Patent
Leonard et al.

(10) Patent No.: US 8,449,621 B2
(45) Date of Patent: May 28, 2013

(54) TEMPORARY IMPLANT INCORPORATING TWO ACTIVE INGREDIENTS

(75) Inventors: Alain Leonard, Caixon (FR); Claudine Lavergne, Caixon (FR); Jean-françois Oglaza, Toulouse (FR)

(73) Assignee: Teknimed, Vic-en-Bigorre (FR)

( * ) Notice: Subject to any disclaimer, the term of this patent is extended or adjusted under 35 U.S.C. 154(b) by 1173 days.

(21) Appl. No.: 11/712,891

(22) Filed: Mar. 2, 2007

(65) Prior Publication Data
US 2008/0058950 A1   Mar. 6, 2008

(30) Foreign Application Priority Data

Mar. 3, 2006 (FR) ...................................... 06 01899

(51) Int. Cl.
*A61F 2/40* (2006.01)
(52) U.S. Cl.
USPC ................ 623/22.4; 623/22.15; 623/23.21; 623/23.44; 623/23.62
(58) Field of Classification Search
USPC ............ 623/22.4, 22.42–22.45, 20.15, 23.36, 623/23.37, 23.19, 23.42
See application file for complete search history.

(56) References Cited

U.S. PATENT DOCUMENTS

| | | | | |
|---|---|---|---|---|
| 4,812,120 | A | * | 3/1989 | Flanagan et al. ............... 433/173 |
| 5,037,442 | A | * | 8/1991 | Wintermantel et al. ....... 433/173 |
| 5,681,289 | A | | 10/1997 | Wilcox et al. |
| 5,968,253 | A | * | 10/1999 | Poser et al. .................... 106/691 |
| 6,245,111 | B1 | | 6/2001 | Shaffner |

FOREIGN PATENT DOCUMENTS

| | | |
|---|---|---|
| DE | 297 03 971 | 7/1998 |
| EP | 1 166 724 | 1/2002 |
| EP | 1 457 172 | 9/2004 |
| WO | WO 01/76512 | 10/2001 |

OTHER PUBLICATIONS

C. Schoellner et al., "Individual bone cement spacers (IBCS) for septic hip revision—preliminary report", *Arch. Orthop. Trauma Surg.*, vol. 123, May 1, 2003, pp. 254-259, XP002408999.
E. Bertazzoni Minelli et al., "Release of gentamicin and vancomycin from temporary human hip spacers in two-stage revision of infected arthroplasty", *Journal of Antimicrobial Chemotherapy*, vol. 53, 2004, pp. 329-334, XP002409000.

* cited by examiner

*Primary Examiner* — David Isabella
*Assistant Examiner* — Yashita Sharma
(74) *Attorney, Agent, or Firm* — Young & Thompson

(57) ABSTRACT

A ready-for-use polymer cement spacer device for the replacement of a permanent joint prosthesis during a two-stage replacement, includes a shank includes for attachment for placing to the supporting bone and a head in the joint region. The spacer device includes two complementary members incorporating rigid members for assembly between them, the first member being loaded with a first active substance and the second member being loaded with a second active substance. The first and second active substances are preferably antibiotics, selected from gentamycin, trobamycin, vancomycin, erythromycin, fucidin, tetracycline or other suitable antibiotics. The temporary joint implant maintains a suitable space for the time necessary for the operation of replacing a permanent prosthesis to prevent tissues from occupying the space released by removal of the permanent prosthesis and ensures effective treatment of resistant infections by local treatment of the joint area through at least two different active substances.

19 Claims, 2 Drawing Sheets

TEMPORARY IMPLANT INCORPORATING TWO ACTIVE INGREDIENTS

This invention relates to the field of temporary joint implants designed to maintain a suitable space for the length of time necessary for the operations of replacing a permanent prosthesis. These temporary implants are also called "spacers".

The invention relates to a ready-for-use spacer device formed from two assembled modules which provide at least two different active substances such as two antibiotics.

BACKGROUND OF THE INVENTION

This application claims the benefit of French Application FR 06 01889, filed Mar. 3, 2006.

In patients fitted with an artificial joint, such as for example a hip prosthesis, it is not rare for it to be necessary to proceed with replacement of the implanted member, either because of mechanical deterioration or because of infectious complications affecting the implant area and giving rise to detachment of the prosthesis. It is then necessary to withdraw the prosthesis and provide antiseptic and antibiotic treatment before replacing a permanent implant. All this operation, known as "two-stage prosthesis replacement" lasts for several weeks, or even several months, because it is essential that the infection should be completely treated by broad spectrum antibiotic treatment associated with local antibiotic treatment before any implant is refitted.

In order to prevent tissues (muscles, tendons, bone) from occupying the space released by removal of the permanent prosthesis, a spacer which temporarily replaces the prosthesis in the joint area is fitted. Thus the risk of the formation of a haematoma and superinfection is reduced, and the limb is better stabilised. Furthermore the patient retains some mobility during the transitional period and ultimately fitting of the permanent prosthesis is made easier.

Spacers are commonly made of relatively cheap materials such as polymer cements, very often polymethyl methacrylate (abbreviated to PPMA). Use of such a polymer has the advantage that it makes it possible for the implant area to be maintained and the infection to be treated locally. In fact because of its cross-linked structure it can be combined with an antibiotic agent which diffuses into the surrounding tissues and thus provides prolonged local treatment for the infection. The antibiotic is progressively released by diffusion in body fluids which are then transported to adjacent tissues.

The antibiotic systematically used in bone surgery is gentamycin, which is a broad spectrum antibiotic. However, given the increase in the level of resistance of bacteria isolated in cases of infection of the hip in particular, recent studies have envisaged the use of a combination of antibiotics in PMMA spacers, such as for example gentamycin and vancomycin (Bertazzoni Minelli E. et al., Journal of Antimicrobial Chemotherapy 2004, 53, pp. 329-334). For this purpose premoulded spaces loaded with commercial gentamycin have been pierced with holes and filled with a cement loaded with vancomycin, this technique making it possible to avoid interference in release of the two antibiotics by the PPMA and adjust the rate of elution for each antibiotic. These tests have demonstrated the effectiveness of combined use of two antibiotics in the local treatment of infections in joint prostheses during two-stage replacements, also with regard to strains which are resistant to conventional treatments. However introduction of the second antibiotic into a spacer which has been preloaded with gentamycin requires difficult manipulation which is hard to reproduce, and which is contrary to safety and quality of care.

SUMMARY OF THE INVENTION

The need for a ready-for-use joint spacer which does not require complex manipulation in the operating theatre and which makes it possible to provide at least two antibiotics for local treatment without substantially increasing manufacturing costs has therefore become apparent. Furthermore it is known that the mixing of powder compounds is difficult and gives rise to homogeneity problems.

The spacer to which this invention relates provides a solution to these requirements while providing a device comprising two complementary parts which can be assembled in one operation to form a complete implant incorporating two different antibiotics which make effective local treatment of infections in the joint area possible.

In addition to the fact that this invention provides a ready-for-use spacer providing at least two different active substances, it also has other advantages deriving from the modular nature of the device. In particular it offers the possibility of choosing the two antibiotics which have to be associated from a range of complementary parts. It also makes it possible to have available a range of spacers of different size, without having to retain a large stock.

Another advantage of the invention is that it provides a spacer which can be mass produced, without lengthening the technological process or making it more burdensome, in such a way that manufacturing costs remain reasonable. In particular it is advantageous to avoid the technological difficulties in the manufacturing process associated with the homogenisation of powder mixtures, the form in which the active substances are generally provided in the cement. This is achieved through this invention by the fact that only one of the active compounds in powder form is added to the ingredients of the cement intended for manufacture of one of the spacer components. The problem of the homogeneous distribution of active substances and that of uniformity in the mechanical properties of the cements obtained is thus reduced. Another advantage of the invention is that mechanical properties and the properties of the cement loaded with the active substance can be easily checked without having to model the behaviour of multiple component mixtures.

Thus this invention relates to a polymer cement spacer device for the replacement of a permanent joint prosthesis during a two-stage replacement comprising a shank which can be attached to the supporting bone and a head which can be placed in the joint region, the said spacer device comprising two complementary parts incorporating rigid means of assembly between them, the first component being loaded with a first active substance and the second component being loaded with a second active substance.

The device according to the invention may take any shape which can be used to provide a temporary spacer, whether known to those skilled in the art at the present time or not, this being largely imposed by the anatomy of the joint requiring treatment. In this application "joint" will designate the unit comprising the adjacent regions of two bones acting together to provide a flexible joint in the skeleton. The joint may be a joint of the hinge type such as the knee, where the ends of the two bones slide over each other during flexion, or a joint of the "cup and ball" type such as the hip. In this case the head of the femur, or ball, is held within the cotyloidal cavity of the bone of the pelvis and slides within the cup. The spacer according to the invention is designed to replace the extremity of a bone, whether the latter acts together with the extremity of another bone or with a cup. As bone repair in the hip is by far the most widespread, this will be specifically described here, although this invention is explicitly intended for the repair of any joint which is capable of receiving a temporary implant. By analogy with anatomical vocabulary, the rounded extremity of the spacer which is intended to replace the end of the bone is referred to as the "head". The shank is the part which is intended to be inserted into the supporting bone, and may also partly replace the latter in order to provide the necessary length. The head and the shank form an assembly, namely the spacer, the junction between them being provided by a simple change in the cross-section of the part, with or without a change in orientation.

The means for assembling the two complementary components of the spacer according to the invention may in principle be located at any point in the spacer, for example the middle of the shank. In a preferred embodiment of the spacer according to the invention the means for assembling the two matching components are located at the junction between the shank and the head of the spacer. This feature provides various advantages which will be more apparent below, such as selection of components according to their size, or changing them, ease of manufacture and fitting, etc.

Advantageously the assembly means are selected from assembly means which are capable of being joined manually, with or without the assistance of a tool. It is thus easy for the surgeon to assemble the spacer from two components instantaneously in a single operation. These assembly means may for example comprise a taper joint, the male cone being preferably borne by the shank and the female cone by the head. When the assembly means are joined together by jamming one component on the other, the force necessary may be provided by a finishing tool such as an impactor. Assembly preferably takes place through simple manual pressure.

In the latter embodiment, according to another useful feature of the spacer according to the invention, the head has symmetry of revolution about the axis of the joint. In fact when assembled the components may be in any relative position. The relative orientation of the two components is determined, when moulding the parts, by the shape of the joint. Thus the surgeon can assemble the spacer very quickly with full confidence in the result of assembly.

As already indicated, the shapes and dimensions of spacers are largely imposed by the anatomy of the joint requiring treatment. As the stature of patients varies, it is useful for the spacer according to the invention to be able to adopt several formats, in particular because the dimensions of the head and the shank can vary independently of each other in order to be associated in all desirable combinations. Thus, particularly when the spacer is intended to be placed in the hip, the shank may be a substantially cylindrical or tapering joint of length between 80 mm and 200 mm. Furthermore the head may form part of a sphere of diameter between 40 mm and 70 mm.

According to a preferred embodiment of the spacer device according to the invention, the shank comprises a metal reinforcement in its core. This reinforcement is able to take up the forces applied to the spacer and stiffen the assembly.

The spacer structure as just described has a number of inherent advantages, in particular as regards the possibility of combining components of different size appropriate to the specific anatomy of individual patients. Thus such spacers can be used as two assembled components, which may be loaded with an active substance or a neutral substance. However, the structure of the two components is essentially designed to be loaded with two active ingredients which it is desired to deliver for local treatment. It should be noted in passing that if there is a need for treatment with three active agents (or even more) it would be wholly possible to produce a polymer spacer formed of three components loaded with three different active substances.

The structure described here is particularly indicated for overcoming the problems of resistant infections by local treatment of the joint area by two different antibiotics. This is why in a particularly preferred embodiment of the spacer according to the invention the first and second active substances are antibiotics. They may in particular be selected from gentamycin, trobamycin, vancomycin, erythromycin, fucidin, tetracycline or other suitable antibiotics.

Advantageously the first active substance is selected from broad spectrum antibiotics and the second active substance is selected from antibiotics having targeted activity. This choice, which is justified by the experience of clinicians, provides the best chance of successful treatment.

According to a particular embodiment the polymer cement comprising the shank advantageously comprises 1.5% to 4.5% of gentamycin by weight with respect to the weight of cement, and preferably approximately 2.3%. Premixtures for the preparation of a cement incorporating gentamycin are commercially available, for example the Gentafix™ cement marketed by the applicant.

Furthermore the polymer cement comprising the head may advantageously comprise vancomycin in a concentration of 0.5% to 3% by weight with respect to the weight of cement, preferably approximately 1.25%.

The two components are preformed and are manufactured from a wholly biocompatible and porous polymer material. Acrylic cements based on methyl polymethylmethacrylate, which are well known to those skilled in the art, because they are commonly used to manufacture commercial one-piece spacers and osteoplasty sealing cements, are wholly suitable for manufacture of the spacer according to the invention.

Such a cement is prepared from a mixture of a prepolymer, generally PMMA (methyl polymethylmethacrylate) and a monomer, generally MMA (methyl methylmethacrylate) which may be accompanied by a co-monomer (butryl), reacting in the presence of a polymerisation activator. They also contain technological additives such as a chemical activator, an initiator, a stabiliser. A radio-opaque substance may also be added so that the spacer becomes visible to radiological means during and after the operation.

Different cements of this type are commercially available. They are commonly presented in the form of two separate components: one powder containing mainly prepolymer beads and a liquid mainly containing the monomer, such as for example the Cemfix™ cement marketed by the applicant. Being used for the manufacture of spacers and for other applications in osteosurgery they meet the requirements for tensile and compressive strength, chemical neutrality and biocompatibility. The additives present in the final cement have no undesirable biological effects. These cements have proved their qualities and are approved for medical use.

The selected antibiotic is incorporated into the powder polymer component in the form of a dry powder and carefully mixed before being combined with the liquid component. During the polymerisation process it is trapped in the molecular network. When the spacer is assembled and installed in the joint, each of the antibiotics will be released progressively in contact with body fluids. The parts are moulded using techniques known to those skilled in the art, for example in silicone moulds.

The antibiotic present in the cement of each spacer component according to the invention will diffuse into nearby tissues to prevent the appearance or spread of infection in the region of the implant. It will be noted that this technique makes it possible to avoid interference with release of the two antibiotics by the PMMA and adjust the rate of elution for each antibiotic separately. Advantageously, the spacer device according to the invention contains a total of between 0.8 g and 1.6 g of gentamycin and between 0.5 g and 1.5 g of vancomycin.

Through this invention a hospital establishment may have available to it a range of heads and shanks containing different antibiotics or other active substances, of different sizes, which can be combined according to need. This modularity enables the care team to select the specific antibiotic for the infection, in the size required, without it being necessary to keep a large stock. Above all, this makes it possible to apply more effective treatment for the patient and to provide care personnel with greater freedom of action, while providing them with very uniform quality material which has no mechanical weaknesses and ensures regular diffusion of the active ingredients. The examples which follow illustrate the invention in order to make its features and advantages more apparent, without in any way reducing its scope.

DETAILED DESCRIPTION OF THE INVENTION

The following abbreviations are used:

| PMMA: | methyl polymethacrylate |
| MMA: | methyl methacrylate |
| BPO: | benzoyl peroxide |
| BaSO$_4$: | barium sulphate |
| DMTP: | dimethyl-paratoluidine |
| HQ: | hydroquinone |

EXAMPLE 1

Hip Spacer Structure

Figure 1:
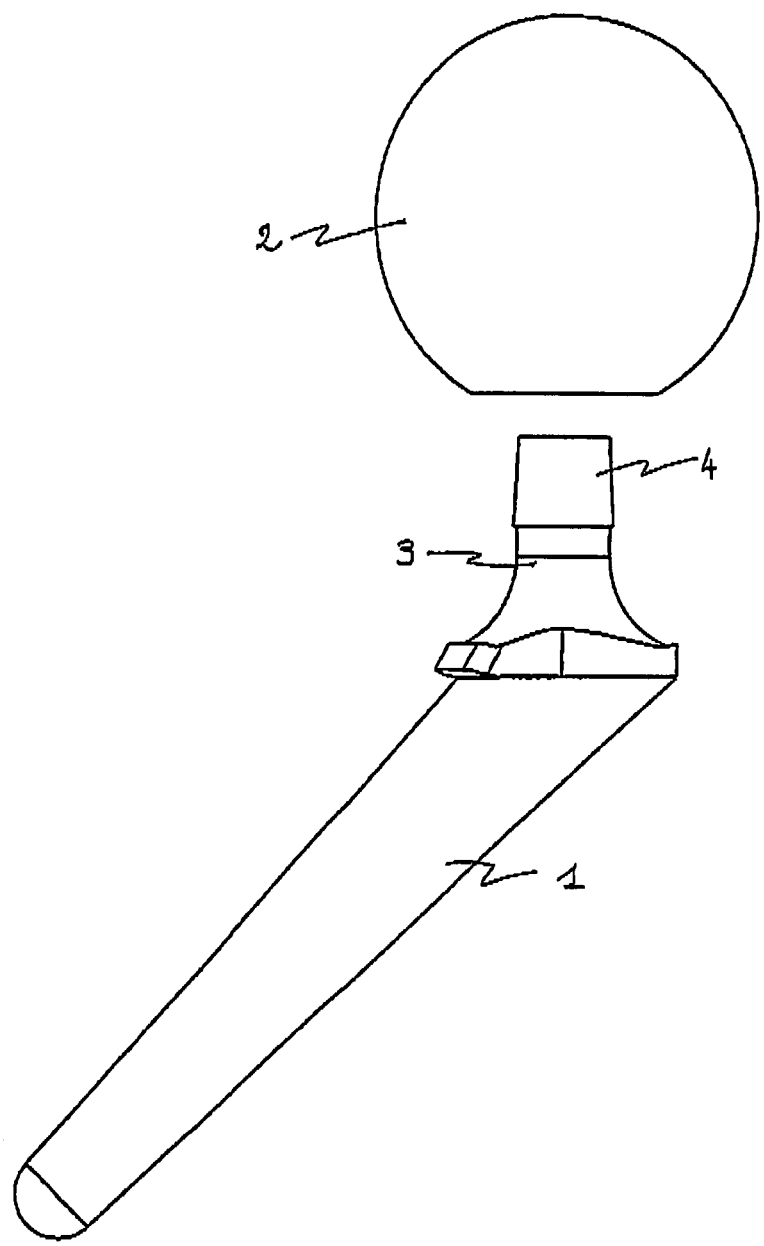
FIG. 1 shows a hip spacer according to the invention before assembly.
Figure 2:
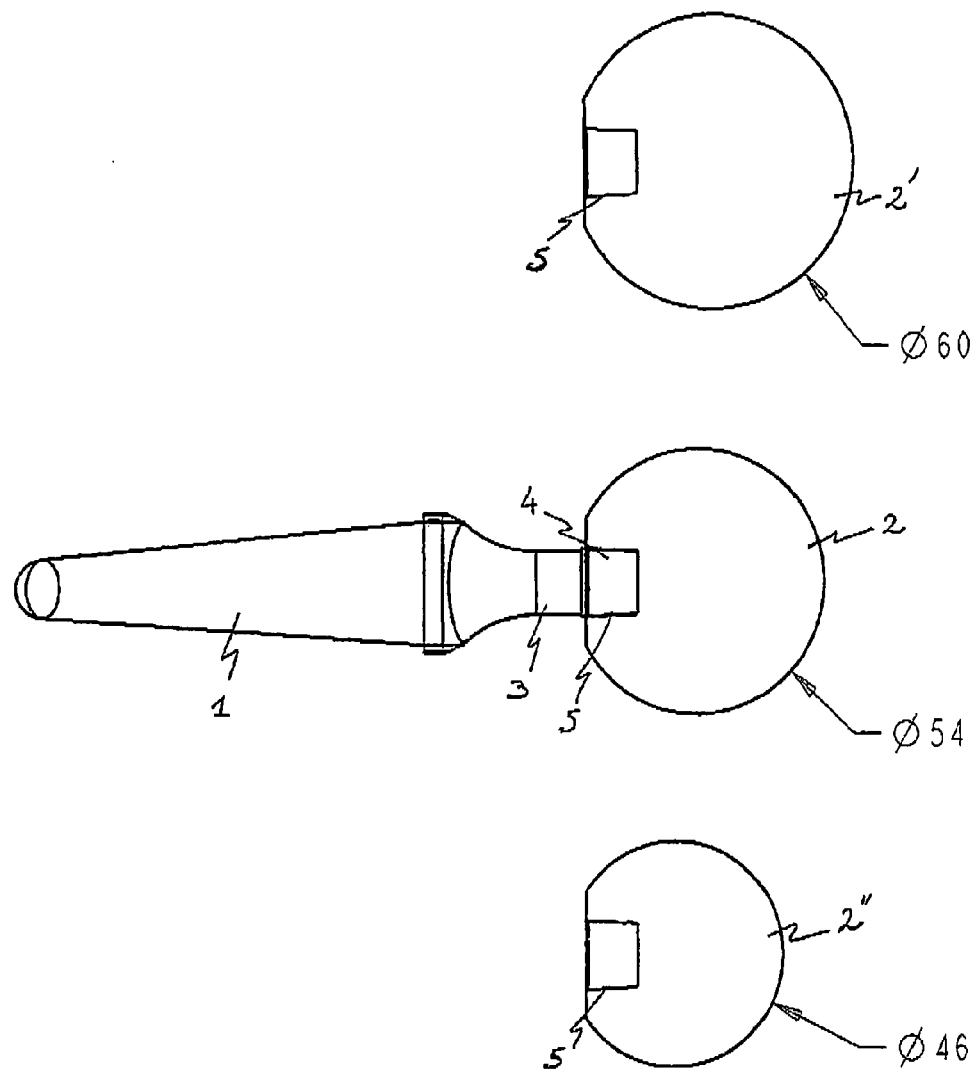
FIG. 2 shows a hip spacer according to the invention after assembly.

The polymer cement spacer device for the replacement of a hip prosthesis as illustrated in FIGS. 1 and 2 comprises:
- shank 1 which is suitable for attachment to the supporting bone, here the femur, comprising a first component loaded with a first active substance, and
- head 2 which is suitable for being located in the joint region, comprising a second component loaded with a second active substance.

These two components are complementary and incorporate rigid means for assembly between them located at the junction 3 between shank 1 and head 2 of the spacer. The assembly means comprise a tapering joint, the male cone 4 being borne by shank 1 and the female cone 4 by head 2, so that the spacer can be assembled by simple manual pressure, or with the aid of an impacter.

Shank 1 is of substantially tapering shape and ends at its proximal extremity in junction 3 bearing male cone 4. It is 120 mm long and has a diameter of 20 mm. It has a metal reinforcement (not shown) of cross-section varying from 6 mm and 10 mm within its core. Head 2 has symmetry of revolution with respect to the axis of the tapering joint. It is inscribed within a sphere of diameter 54 mm (2) or alternatively 60 mm (2') or 46 mm (2").

EXAMPLE 2

Composition of a Cement C1

Composition C1 corresponds to a polymer cement containing gentamycin in the form of sulphate as a broad spectrum antibiotic.

| POWDER PHASE | (% by weight) | LIQUID PHASE | (% by weight) |
|---|---|---|---|
| PMMA: | 84.3% | MMA: | 84.4% |
| BPO: | 2.3% | Butryl: | 13.2% |
| BaSO$_4$: | 9.6% | DMPT: | 2.4% |
| Gentamycin sulphate: | 3.8% | HQ: | 20 ppm |

The cement is prepared by mixing 40 kg of powder phase with 25 kg of liquid phase in a reactor. When the mixture is uniform and of a creamy consistency it is poured into the manufacturing moulds. After drying and turning out, the parts are trimmed. They can then be sterilised and packed in a known way.

Parts containing gentamycin in a concentration of 2.34% by weight are obtained.

EXAMPLE 3

Composition of a Cement C2

Composition C2 corresponds to a polymer cement containing vancomycin as a targeted action antibiotic. It acts on microorganisms such as Gram positive aerobic species (*Bacilli, Enterococci, Lysteria rhodococcus equi, Staphylococcus aureus*, non-aureus *Staphylococci, Streptococci* in particular *Streptococcus pneumonia*), and anaerobic species (*Clostridium, Eubacterium, Peptostreptococci, Propionibacterium acnes*).

| POWDER PHASE | (% by weight) | LIQUID PHASE | (% by weight) |
|---|---|---|---|
| PMMA: | 87.6% | MMA: | 84.4% |
| BPO: | 2.4% | Butryl: | 13.2% |
| BaSO$_4$: | 10.0% | DMPT: | 2.4% |
| Vancomycin: | 4.8% | HQ: | 20 ppm |

Cement C2 is prepared using the same protocol as that described above for Example 2, using 42 kg of powder phase and 25 kg of liquid phase.

Parts containing vancomycin in a concentration of 1.25% are obtained.

EXAMPLE 4

Composition of a Cement C3

Composition C3 corresponds to a polymer cement containing trobamycin as a targeted action antibiotic. It acts on microorganisms such as Gram positive aerobic species (*Corynebacterium, Listeria monocytogenes*, methicillin-sensitive *Staphylococcus aureus*, methicillin-sensitive coagulase-negative *Staphylococci*), and on Gram negative aerobic species (*Acinobacter*, in particular *A. boumanii, Branhamella catarrhalis, Campylobacter, Citrobacter freundii, Citrobacter koseri, Enterobacter aerogenes, Enterobacter cloacae, Escherichia coli, Haemophilus influenzae, Klebsiella, Morganella morganii, Proteus mirabilis, Proteus vulgaris, Pseudomonas aeruginosa, Salmonella, Serratia, Shigella, Yersinia*)

| POWDER PHASE | (% by weight) | LIQUID PHASE | (% by weight) |
|---|---|---|---|
| PMMA: | 87.6% | MMA: | 84.4% |
| BPO: | 2.4% | Butyryl: | 13.2% |
| BaSO$_4$: | 10.0% | DMPT: | 2.4% |
| Trobamycin: | 4.8% | HQ: | 20 ppm |

Cement C3 is prepared as described above for Example 2, using 42 kg of powder phase and 25 kg of liquid phase.

Parts containing trobamycin in a concentration of 1.25% by weight are obtained.

EXAMPLE 5

Hip Spacer E1

Hip spacer E1 is constructed using a shank obtained from cement C1 containing gentamycin and a head obtained from cement C2 containing vancomycin. Diffusion tests have been carried out.

The diffusion kinetics of gentamycin are well known to those skilled in the art because this antibiotic is already administered using conventional one-piece spacers. These take the form of a major input during the first few hours and then slow release over the next two weeks following implant, remaining almost constant thereafter for several weeks. This "flash" effect is beneficial for an effective start to treatment.

Tests performed on the diffusion of vancomycin have shown that 3% of the initial vancomycin is released after the spacer has been implanted for one week, including 15 mg on the first day, 3 mg on the second day and 1.3 mg on the third day. After 6 months 8% of the vancomycin has been diffused out.

In general tests show that vancomycin diffuses satisfactorily into the joint space. Furthermore, if the powder mixture is carefully prepared, virtually no deterioration of the cement from a mechanical point of view is observed.

The invention claimed is:

1. A cement spacer device for the replacement of a permanent joint prosthesis in the case of a two-stage replacement, said cement spacer device comprising:
    a first and a second complementary component, and
    an incorporating rigid member for assembly between said first and second components,
    the first complementary component being loaded with a first active substance and the second complementary component being loaded with a second active substance different from said first active substance.

2. The cement spacer device according to claim 1, wherein the first and second active substances are antibiotics.

3. The cement spacer device according to claim 2, wherein the first and second active substances are antibiotics selected from the group consisting of: gentamycin, trobamycin, erythromycin, vancomycin, fucidin, and tetracycline.

4. The cement spacer device according to claim 3, wherein the first active substance is selected from a broad spectrum antibiotics and the second active substance is selected from antibiotics having targeted activity.

5. The cement spacer device according to claim 1, wherein said first component is a shank adapted to attach to a supporting bone and said second component is a head adapted to be located in a joint region.

6. The cement spacer device according to claim 5, wherein the incorporating rigid member for assembly is located at a junction between the shank and the head.

7. The cement spacer device according to claim 6, wherein the incorporating rigid member for assembly is adapted to being joined manually, with or without the assistance of a tool.

8. The cement spacer device according to claim 6, wherein the shank has a metal reinforcement in its core.

9. The cement spacer device according to claim 6, wherein the first and second active substances are antibiotics.

10. The cement spacer device according to claim 6, further comprising 0.8 g to 1.6 g of gentamycin and 0.5 g to 1.5 g of vancomycin.

11. The cement spacer device according to claim 5, wherein the incorporating rigid member for assembly is adapted to be joined manually, with or without the assistance of a tool.

12. The cement spacer device according to claim 11, wherein the head has a symmetry of revolution in relation to an axis of a junction between the shank and the head.

13. The cement spacer device according to claim 5, wherein the head has a symmetry of revolution in relation to an axis of the junction.

14. The cement spacer device according to claim 5, wherein the shank has a metal reinforcement in its core.

15. The cement spacer device according to claim 5, wherein the shank comprises a polymer cement containing 1.5% to 4.5% of gentamycin by weight in relation to the weight of the cement.

16. The cement spacer device according to claim 15, wherein the polymer cement comprises 2.3% gentamycin by weight.

17. The cement spacer device according to claim 5, wherein the head comprises a polymer cement containing 0.5% to 3% of vancomycin by weight with respect to the weight of the cement.

18. The cement spacer device according to claim 17, wherein the polymer cement comprises 1.25% vancomycin by weight.

19. The cement spacer device according to claim 5, further comprising 0.8 g to 1.6 g of gentamycin and 0.5 g to 1.5 g of vancomycin.

* * * * *